US009708191B2

(12) United States Patent
Iwanaga et al.

(10) Patent No.: US 9,708,191 B2
(45) **Date of Patent: *Jul. 18, 2017**

(54) SILICA COMPOSITE PARTICLES AND METHOD OF PREPARING THE SAME

(71) Applicant: FUJI XEROX CO., LTD., Tokyo (JP)

(72) Inventors: Takeshi Iwanaga, Kanagawa (JP); Yuka Zenitani, Kanagawa (JP); Yoshifumi Iida, Kanagawa (JP); Daisuke Tomita, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 354 days.

This patent is subject to a terminal disclaimer.

(21) Appl. No.: 14/555,957

(22) Filed: Nov. 28, 2014

(65) Prior Publication Data

US 2015/0075083 A1 Mar. 19, 2015

Related U.S. Application Data

(62) Division of application No. 13/670,040, filed on Nov. 6, 2012, now abandoned.

(30) Foreign Application Priority Data

Dec. 1, 2011 (JP) ................................ 2011-264067
Jul. 13, 2012 (JP) ................................ 2012-158114

(51) Int. Cl.

| | |
|---|---|
| ***C01B 33/18*** | (2006.01) |
| ***C09K 3/14*** | (2006.01) |
| ***C07F 7/28*** | (2006.01) |
| ***B82Y 30/00*** | (2011.01) |
| ***C01B 33/12*** | (2006.01) |
| ***C09C 1/28*** | (2006.01) |
| ***C09C 1/30*** | (2006.01) |

(52) U.S. Cl.

CPC .............. *C01B 33/18* (2013.01); *B82Y 30/00* (2013.01); *C01B 33/12* (2013.01); *C07F 7/28* (2013.01); *C09C 1/28* (2013.01); *C09C 1/309* (2013.01); *C09C 1/3045* (2013.01); *C09C 1/3081* (2013.01); *C09K 3/1436* (2013.01); *C01P 2002/54* (2013.01); *C01P 2004/32* (2013.01); *C01P 2004/51* (2013.01); *C01P 2004/62* (2013.01); *C01P 2004/64* (2013.01); *Y10S 977/773* (2013.01); *Y10S 977/896* (2013.01); *Y10T 428/2982* (2015.01)

(58) Field of Classification Search

None
See application file for complete search history.

(56) References Cited

U.S. PATENT DOCUMENTS 4,775,520 A 10/1988 Unger et al.
4,849,390 A 7/1989 Sano et al.
4,902,598 A 2/1990 Winnik et al.
4,911,903 A 3/1990 Unger et al.
5,221,497 A 6/1993 Watanabe et al.
5,597,512 A 1/1997 Watanabe et al.
5,609,675 A 3/1997 Noritake et al.
5,674,589 A 10/1997 Bennett et al.
5,985,229 A 11/1999 Yamada et al.
5,998,329 A 12/1999 Derolf et al.
6,113,682 A 9/2000 Shin et al.
6,403,271 B1 6/2002 Suzuki et al.
6,770,130 B2 8/2004 Kato et al.
6,811,944 B2 11/2004 Higuchi et al.
6,875,549 B2 4/2005 Yamazaki et al.
7,846,632 B2 12/2010 Nakatani
2003/0133890 A1* 7/2003 Kato ...................... B82Y 30/00 424/59
2004/0067189 A1 4/2004 Sugiura et al.
2004/0137353 A1 7/2004 Iida et al.
2004/0222618 A1 11/2004 Azechi et al.
2004/0229040 A1 11/2004 Kudo et al.
2005/0260515 A1 11/2005 Kato et al.
2007/0020543 A1 1/2007 Nakatani
2007/0218387 A1 9/2007 Ishii et al.
2008/0086951 A1 4/2008 Wakamiya et al.
(Continued)

FOREIGN PATENT DOCUMENTS

CN 86106689 A 5/1987
CN 1380585 A 11/2002
(Continued)

OTHER PUBLICATIONS

Office Action issued in Australian Patent Application No. 2012258292 dated Jul. 22, 2013.
Apr. 12, 2012 Extended European Search Report issued in European Patent Application No. 11185668.8.
Aug. 16, 2013 Office Action issued in U.S. Appl. No. 13/214,816.
Dec. 19, 2013 Office Action issued in Chinese Application No. 201010546805.8 (with English Translation).
Jan. 30, 2014 Office Action issued in U.S. Appl. No. 13/214,657.
Jan. 30, 2014 Office Action issued in U.S. Appl. No. 13/214,816.
(Continued)

*Primary Examiner* — Alexandre Ferre
(74) *Attorney, Agent, or Firm* — Oliff PLC

(57) ABSTRACT

A method of preparing silica composite particles includes preparing an alkali catalyst solution containing an alkali catalyst at a concentration of from 0.6 mol/L to 0.85 mol/L, in a solvent containing alcohol; and supplying, into the alkali catalyst solution, (i) a mixed solution of tetraalkoxysilane and an organic titanium compound in which an organic group is coupled to a titanium atom through oxygen, and (ii) an alkali catalyst. The mixed solution is supplied at a supply amount of from 0.001 mol/(mol·min) to 0.01 mol/(mol·min) relative to the alcohol, and the alkali catalyst is supplied at a supply amount of from 0.1 mol to 0.4 mol, relative to 1 mol of a total supply amount of the tetraalkoxysilane and the organic titanium compound supplied per one minute.

7 Claims, No Drawings

(56) References Cited

U.S. PATENT DOCUMENTS

| | | | |
|---|---|---|---|
| 2008/0268362 | A1 | 10/2008 | Kudo |
| 2009/0196658 | A1 | 8/2009 | Sugiura |
| 2010/0104323 | A1 | 4/2010 | Toizumi et al. |
| 2010/0203443 | A1 | 8/2010 | Okita et al. |
| 2010/0330488 | A1 | 12/2010 | Ieda |
| 2011/0209413 | A1 | 9/2011 | Nishida et al. |
| 2011/0318581 | A1* | 12/2011 | Zenitani ................ C01B 33/145 428/402 |
| 2011/0318584 | A1 | 12/2011 | Yoshikawa et al. |
| 2011/0319647 | A1 | 12/2011 | Yoshikawa et al. |

FOREIGN PATENT DOCUMENTS

| | | |
|---|---|---|
| CN | 101271287 A | 9/2008 |
| EP | 0 574 642 A1 | 12/1993 |
| JP | A-62-52119 | 3/1987 |
| JP | A-1-317115 | 12/1987 |
| JP | A-63-310714 | 12/1988 |
| JP | A-1-317115 | 12/1989 |
| JP | A-4-187512 | 7/1992 |
| JP | A-4-238807 | 8/1992 |
| JP | A-04-255755 | 9/1992 |
| JP | A-5-48152 | 1/1993 |
| JP | A-06-041419 | 2/1994 |
| JP | A-6-254383 | 9/1994 |
| JP | A-7-118008 | 5/1995 |
| JP | A-7-277725 | 10/1995 |
| JP | A-8-12305 | 1/1996 |
| JP | A-08-283617 | 10/1996 |
| JP | A-09-143401 | 6/1997 |
| JP | A-9-202612 | 8/1997 |
| JP | A-11-60232 | 3/1999 |
| JP | A-11-286611 | 10/1999 |
| JP | A-2000-344512 | 12/2000 |
| JP | A-2001-150334 | 6/2001 |
| JP | A-2001-189009 | 7/2001 |
| JP | A 2002-038049 | 2/2002 |
| JP | A-2002-38049 | 2/2002 |
| JP | A-2002-146233 | 5/2002 |
| JP | A-2003-133267 | 5/2003 |
| JP | A-2003-165718 | 6/2003 |
| JP | A-2003-171117 | 6/2003 |
| JP | A-2004-35293 | 2/2004 |
| JP | A-2004-102236 | 4/2004 |
| JP | A-2004-203638 | 7/2004 |
| JP | A 2004-203638 | 7/2004 |
| JP | A-2004-338969 | 12/2004 |
| JP | A-2005-84295 | 3/2005 |
| JP | A-2006-028319 | 2/2006 |
| JP | A-2007-22827 | 2/2007 |
| JP | A-2008-169102 | 7/2008 |
| JP | A-2008-174430 | 7/2008 |
| JP | A-2008-285406 | 11/2008 |
| JP | A 2009-078935 | 4/2009 |
| JP | A-2009-78935 | 4/2009 |
| JP | A-2009-137791 | 6/2009 |
| JP | A-2009-149493 | 7/2009 |
| JP | A-2009-161371 | 7/2009 |
| JP | A-2009-186512 | 8/2009 |
| JP | A-2010-107601 | 5/2010 |
| JP | A-2011-185998 | 9/2011 |
| JP | A-2012-6781 | 1/2012 |
| JP | A-2012-6789 | 1/2012 |
| WO | WO 2008/018966 A2 | 2/2008 |
| WO | WO 2010/052945 A1 | 5/2010 |

OTHER PUBLICATIONS

Jul. 19, 2013 Office Action issued in U.S. Appl. No. 13/214,657.
Kim et al., "Influence of reaction conditions on sol-precipitation process producing silicon oxide particles," Ceramics International, vol. 28 (2002), pp. 187-194.
Mar. 14, 2013 Office Action issued in U.S. Appl. No. 12/912,057.
Mar. 20, 2013 Office Action issued in U.S. Appl. No. 12/917,814.
Nagao et al., "Particle formation in the hydrolysis of tetraethyl orthosilicate in pH buffer solution," Journal of Colloid and Interface Science, vol. 279 (2004), pp. 143-149.
Oct. 15, 2013 Office Action issued in Japanese Application No. 2010-143828 (with English Translation).
Oct. 23, 2012 Office Action issued in U.S. Appl. No. 12/912,057.
Oct. 29, 2013 Office Action issued in Japanese Patent Application No. 2010-145221 (with English Translation).
Sep. 10, 2012 Australian Office Action issued in Australian Patent Application No. 2011232772.
Sep. 17, 2012 Office Action issued in U.S. Appl. No. 12/917,814.
U.S. Appl. No. 12/912,057 in the name of Zenatani et al. filed Oct. 26, 2010.
U.S. Appl. No. 12/917,814 in the name of Yoshikawa et al. filed Nov. 2, 2010.
U.S. Appl. No. 13/214,657 in the name of Zenitani et al. filed Aug. 22, 2011.
U.S. Appl. No. 13/214,816 in the name of Yoshikawa et al. filed Aug. 22, 2011.
Wang et al., "Preparation of spherical silica particles by Stöber process with high concentration of tetra-ethyl-orthosilicate," Journal of Colloid and Interface Science, vol. 341, pp. 23-29, available online Sep. 18, 2009.
U.S. Appl. No. 13/934,928 in the name of Iwanaga et al., filed Jul. 3, 2013.
May 7, 2014 Office Action issued in U.S. Appl. No. 12/917,814.
May 23, 2014 Notice of Allowance issued in U.S. Appl. No. 12/912,057.
Aug. 20, 2014 Office Action issued in Chinese Application No. 201010546805.8 (with English Translation).
Other Document 1: Table to confirm that the oxide particles described in [Table 1] of [0265] of Publication 1 satisfy the formula (1) of Claim 1 of the present application (with English Translation).
Jul. 7, 2014 Information Offer Form issued in Japanese Application No. 2011-008842 (with English Translation).
Aug. 11, 2014 Notice of Information Offer issued in Japanese Patent Application No. 2011-010052 w/translation.
U.S. Appl. No. 13/670,040 in the name of Iwanaga et al. filed Nov. 6, 2012.

* cited by examiner

SILICA COMPOSITE PARTICLES AND METHOD OF PREPARING THE SAME

This is a divisional of application Ser. No. 13/670,040 filed Nov. 6, 2012, and claims priority to Japanese Patent Applications No. 2011-264067 filed Dec. 1, 2011 and No. 2012-158114 filed Jul. 13, 2012. The entire disclosure of the prior applications are hereby incorporated by reference in their entirety.

BACKGROUND

1. Technical Field

The present invention relates to silica composite particles and a method of preparing the same.

2. Related Art

Silica particles are used as additives or main ingredients of toners, cosmetics, rubbers, abrasives and the like, and have a role of, for example, improving the strength of resins, improving the fluidity of powders, or suppressing packing. Since it is considered that the properties of the silica particles are likely to depend on the shape of the silica particles, silica particles having various shapes have been proposed.

SUMMARY

According to an aspect of the invention, there is provided silica composite particles including silicon oxide; and titanium in an amount of from 0.001% by weight to 10% by weight, wherein the silica composite particles have an average particle diameter of from 30 nm to 500 nm, a particle size distribution index of from 1.1 to 1.5, and an average degree of circularity of primary particles of from 0.5 to 0.85.

DETAILED DESCRIPTION

Hereinafter, an exemplary embodiment illustrating an example of the invention will be described in detail.

Silica Composite Particles

The silica composite particles according to the exemplary embodiment include silicon oxide and titanium having a content (the content in the entire silica composite particles) being from 0.001% by weight to 10% by weight.

In addition, the silica composite particles according to the exemplary embodiment have an average particle diameter of from 30 nm to 500 nm, a particle size distribution index of from 1.1 to 1.5, and an average degree of circularity of from 0.5 to 0.85.

Due to the aforementioned configuration, the silica composite particles according to the exemplary embodiment suppress deterioration of the dispersibility into a target to be attached (for example, resin particles, iron powder and other powder) and the maintenance of fluidity of the target to be attached even if the temperature and humidity environment fluctuates.

The reason for this is not clear, but is considered to be as follows.

The silica composite particles having the volume average particle diameter, the particle size distribution index and the average degree of circularity are the particles having the characteristics that the particle size distribution is uniform in an appropriate range, and moreover, have an irregular shape having more unevenness as compared with a real sphere.

Since such silica composite particles have uniform particle size distribution in an appropriate range, the adhesion among the particles is considered to be lower and thus less likely to cause friction among the particles, as compared with particles having a broader particle size distribution. As a result, it is considered that the silica composite particles per se are excellent in fluidity.

Furthermore, it is considered that since the silica composite particles have an irregular shape in an appropriate size, in a case of being attached to a target to be attached, occurrence of uneven distribution or deviation caused by embedding into the target to be attached or rolling is suppressed, and occurrence of destruction caused by a mechanical load is suppressed, as compared with a case of a spherical shape (a shape having an average degree of circularity greater than 0.85).

Therefore, it is considered that the silica composite particles according to the exemplary embodiment suppress deterioration of the dispersibility into a target to be attached and the maintenance of fluidity of a target to be attached.

In addition, since the silica composite particles of the exemplary embodiment contain titanium in an appropriate range, hygroscopicity decreases, as compared with the silica particles including only silicon oxide, that is, when the temperature and humidity environment has fluctuated (for example, environmental fluctuation between the environment of high temperature and high humidity represented by the summer environment and the environment of low temperature and low humidity represented by the winter environment), the fluctuation of the amount of water retention decreases, and especially, it is considered that the fluctuations of the characteristics (such as fluidity of the silica composite particles per se) are suppressed.

From the above, it is considered that the silica composite particles according to the exemplary embodiment suppress deterioration of the dispersibility into a target to be attached and the maintenance of fluidity of a target to be attached even if the temperature and humidity environment fluctuates.

Hereinafter, the silica composite particles according to the exemplary embodiment will be described in detail.

The silica composite particles according to the exemplary embodiment are composite particles in which silicon oxide (silicon dioxide:silica) has been mixed with titanium, in other words, composite particles in which titanium is present in a dispersed state in particles including silicon oxide.

In addition, the content of titanium in the entire silica composite particles is from 0.001% by weight to 10% by weight, preferably from 0.01% by weight to 9% by weight, and more preferably from 0.1% by weight to 5% by weight.

When the content of titanium is less than 0.001% by weight, the fluctuations of the characteristics of the silica composite particles caused by the temperature and humidity environmental fluctuations occur.

On the other hand, when the content of titanium exceeds 10% by weight, in a case of manufacturing the silica composite particles, this causes the vigorous reaction of an organic titanium compound (particularly, tetraalkoxytitanium), which leads to excess occurrence of coarse powder or the deterioration of particle size distribution and of the shape, thereby the desired particle size is unable to be obtained. In particular, in a case where a mechanical load is applied to the silica composite particles, the particles tend to have defects, and it is difficult to have an improvement in fluidity maintenance.

The measurement of the content of titanium is performed by obtaining the NET strength of constitutional elements in the particles, using a fluorescence X-ray analyzer: XRF1500 (manufactured by Shimadzu Corporation), and quantifying the titanium content from the standard curve of the above NET strength and NET strengths at titanium contents of 0% and 100%.

Average Particle Diameter

The silica composite particles according to the exemplary embodiment have an average particle diameter of from 30 nm to 500 nm, preferably from 60 nm to 500 nm, more preferably from 100 nm to 350 nm, and still more preferably from 100 nm to 250 nm.

In addition, the average particle diameter is the average particle diameter of the primary particles of the silica composite particles.

When the average particle diameter of the silica composite particles is less than 30 nm, the shape of the silica composite particles tends to be spherical, and it is difficult to have a shape having an average degree of circularity of the silica composite particles from 0.50 to 0.85. In addition, even if the particles have an irregular shape, this makes it difficult to suppress the embedding of the silica composite particles into a target to be attached, and makes it difficult to realize the maintenance of fluidity of a target to be attached.

On the other hand, when the average particle diameter of the silica composite particles exceeds 500 nm, in a case where a mechanical load is applied to the silica composite particles, the particles tend to have defects, which makes it difficult to realize the maintenance of fluidity of a target to be attached.

In regard to measuring the average particle diameter of the silica composite particles, the silica composite particles are dispersed into resin particles having a particle size of 100 μm (polyester, weight average molecular weight Mw=50000), and then 100 primary particles of the dispersed silica composite particles are observed with an SEM (Scanning Electron Microscope) apparatus. The average particle diameter means a 50% diameter (D50v) in the cumulative frequency of the circle-equivalent diameter obtained by an image analysis for the primary particles.

Particle Size Distribution Index

The silica composite particles according to the exemplary embodiment have a particle size distribution index of from 1.1 to 1.5, preferably from 1.25 to 1.40.

In addition, the particle size distribution index is the particle size distribution index of the primary particles of silica composite particles.

The silica particles in which the particle size distribution index of the silica composite particles is less than 1.1 are difficult to be prepared.

On the other hand, when the particle size distribution of the silica composite particles exceeds 1.5, coarse particles occur, or the dispersibility into a target to be attached deteriorates due to variations in particle size. In addition, with the increase of the presence of the coarse particles, number of defects in the particles increases due to mechanical loads thereof, thereby making it difficult to realize the fluidity maintenance of a target to be attached.

In regard to measuring a particle size distribution index of the silica composite particles, the silica composite particles are dispersed into resin particles having a particle size of 100 μm (polyester, weight average molecular weight Mw=50000), and then 100 primary particles of the dispersed silica composite particles are observed with an SEM apparatus. The particle size distribution index means the square root of the value obtained by dividing an 84% diameter by a 16% diameter in the cumulative frequency of the circle-equivalent diameter obtained by an image analysis for the primary particles.

Average Degree of Circularity

The silica composite particles according to the exemplary embodiment have an average degree of circularity of the primary particles of from 0.5 to 0.85, preferably from 0.6 to 0.8.

In addition, the average degree of circularity is the average degree of circularity of the primary particles of the silica composite particles.

When the average degree of circularity of the silica composite particles is less than 0.50, the particles have a spherical shape with a large vertical/horizontal ratio of the silica composite particles. As a result, in a case where a mechanical load is applied to the composite silica particles, stress concentration occurs, thereby the particles tend to have defects, which makes it difficult to realize the maintenance of fluidity of a target to be attached.

On the other hand, when the average degree of circularity of the silica composite particles exceeds 0.85, the silica composite particles approach a spherical shape. Therefore, in a case of mixing with a target to be attached, due to the mechanical loads such as stirring, the silica composite particles may be unevenly attached, or after being stored over time, the silica composite particles may be unevenly attached, and thus the dispersibility into the target to be attached deteriorates, and additionally, the silica composite particles tend to be detached from the target to be attached.

In relation to the degree of circularity "100/SF2" of the silica composite particles, the silica composite particles are dispersed into resin particles having a particle size of 100 μm (polyester, weight average molecular weight Mw=50000), and then primary particles of the dispersed silica particles are observed with an SEM apparatus. The degree of circularity is calculated by the following formula from an image analysis for the obtained primary particles.

$$\text{Degree of Circularity}(100/SF2)=4\pi\times(A/I^2) \qquad \text{Formula (1)}$$

In Formula (1), I represents a peripheral length of the primary particles shown on the images, and A represents a projected area of the primary particles.

In addition, the average degree of circularity of the silica composite particles is obtained as a 50% degree of circularity in the cumulative frequency of the circle-equivalent diameters of 100 primary particles obtained by the image analysis.

Method of Preparing Silica Composite Particles

The method of preparing the silica composite particles according to the exemplary embodiment is an example of the preparation method for obtaining the silica composite particles according to the exemplary embodiment described above, and is specifically as follows.

The method of preparing the silica composite particles according to the exemplary embodiment is a method of preparing silica composite particles including: preparing an alkali catalyst solution containing an alkali catalyst at a concentration of from 0.6 mol/L to 0.85 mol/L, in a solvent containing alcohol; and supplying, into the alkali catalyst solution, a mixed solution of tetraalkoxysilane and an organic titanium compound in which an organic group is coupled to a titanium atom through oxygen at a supply amount of from 0.001 mol/(mol·min) to 0.01 mol/(mol·min) relative to the alcohol, and an alkali catalyst at a supply amount of from 0.1 mol to 0.4 mol, relative to 1 mol of a total supply amount of the tetraalkoxysilane and the organic titanium compound supplied per one minute.

In addition, hereafter, the "mixed solution of tetraalkoxysilane and the organic titanium compound", is referred to as "organic metal mixed solution", and "tetraalkoxysilane and the organic titanium compound" are referred to as "organic metal compound", generically.

That is, the method of preparing the silica composite particles according to the exemplary embodiment is a method of generating the silica composite particles by allowing organic metal compounds to react, respectively, in the presence of alcohol containing an alkali catalyst at the aforementioned concentration, while separately supplying an organic metal mixed solution as a raw material and an alkali catalyst as a catalyst in the amounts that satisfy the aforementioned relationship.

In the method of preparing the silica composite particles according to the exemplary embodiment, the occurrence of coarse aggregates is reduced and irregularly shaped silica composite particles are obtained, by the technique described above. The reason for this is not clear, but is considered to be as follows.

First, an alkali catalyst solution in which an alkali catalyst is contained in a solvent containing alcohol is prepared. When an organic metal mixed solution and an alkali catalyst are supplied to this solution, respectively, the organic metal compounds supplied to the alkali catalyst solution are allowed to react, respectively, and nuclear particles are generated. At this time, when the concentration of the alkali catalyst in the alkali catalyst solution is within the range as defined above, it is considered that nuclear particles having an irregular shape may be generated while suppressing generation of coarse aggregates such as secondary aggregates. This is considered to be based on the following reason. In addition to catalytic action thereof, the alkali catalyst coordinates with the surface of the nuclear particles that are generated and contributes to the shape and dispersion stability of the nuclear particles. However, when the amount is in the range described above, the alkali catalyst does not uniformly cover the surface of the nuclear particle (that is, the alkali catalyst is unevenly distributed on the surface of the nuclear particles and adheres to the surface). Accordingly, even though the dispersion stability of the nuclear particles is maintained, partial bias in the surface tension, and chemical affinity of the nuclear particles occur, and thus irregular shaped nuclear particles are generated.

When the supplies of the organic metal mixed solution and the alkali catalyst are respectively continued, the nuclear particles that are generated grow as a result of the respective reactions of the organic metal compounds, and thereby the silica composite particles are obtained.

It is considered that when these supplies of the organic metal mixed solution and the alkali catalyst are carried out while the amounts of supply are set to be in the relationship described above, the irregular shaped nuclear particles grow into particles while maintaining the irregular shape, with the generation of coarse aggregates such as secondary aggregates being suppressed, and as a result, irregular shaped silica composite particles are generated. This is considered to be because, when these amounts of supply of the organic metal mixed solution and the alkali catalyst are maintained in the relationship described above, the dispersion of the nuclear particles is maintained, while the partial bias in the tension and chemical affinity at the nuclear particle surface is maintained, and therefore, the nuclear particles grow into particles while maintaining the irregular shape.

Here, it is considered that the supply amount of the organic metal mixed solution has effects on the particle size distribution or the degree of circularity of the silica composite particles. It is considered that, by controlling the supply amount of the organic metal mixed solution to be from 0.001 mol/(mol·min) to 0.01 mol/(mol·min) relative to the alcohol, the contact probability of the metal alkoxides added dropwise and the nuclear particles is reduced, and the organic metal compound are evenly supplied to the nuclear particles before the organic metal compounds react with each other. Thus, it is considered that the reaction of the organic metal compound with the nuclear particles can evenly take place. As a result, it is considered that the variation in particle growth may be suppressed and the silica composite particles having a narrow distribution width may be prepared.

In addition, it is considered that the average particle diameter of the silica composite particles depends on the total supply amount of the organic metal compound.

From the above, it is considered that in the method of preparing the silica composite particles according to the exemplary embodiment, the silica composite particles according to the exemplary embodiment described above may be obtained.

Furthermore, it is considered that in the method of preparing the silica composite particles according to the exemplary embodiment, irregular shaped nuclear particles are generated, and the nuclear particles are allowed to grow while maintaining this irregular shape, to thereby generate the silica composite particles. Therefore, it is considered that irregular shaped silica composite particles having high shape-stability against a mechanical load, are obtained.

Furthermore, it is considered that in the method of preparing the silica composite particles according to the exemplary embodiment, the generated irregular shaped nuclear particles grow into particles while maintaining the irregular shape, and thus the silica composite particles are obtained. Therefore, it is considered that the silica composite particles that are strong against a mechanical load and are difficult to break, are obtained.

Furthermore, in the method of preparing the silica composite particles according to the exemplary embodiment, when a mixed solution of alkoxysilane and the organic titanium compound and an alkali catalyst are respectively supplied into an alkali catalyst solution, the respective reactions of alkoxysilane and the organic titanium compound are induced, and thereby the generation of particles is achieved. Therefore, the total amount of the alkali catalyst used is reduced as compared with the case of preparing irregular shaped silica composite particles by a sol-gel method in the related art, and as a result, the omission of a step for the removal of alkali catalyst is also realized. This is favorable in the case of applying the silica composite particles to a product where high purity is required.

First, an alkali catalyst solution preparing step will be described.

The alkali catalyst solution preparing step includes preparing a solvent containing alcohol, and adding an alkali catalyst to this solvent, thereby preparing an alkali catalyst solution.

The solvent containing alcohol may be formed only of alcohol, or may be a mixed solvent combined with other solvents, including water, ketones such as acetone, methyl ethyl ketone or methyl isobutyl ketone, cellosolves such as methyl cellosolve, ethyl cellosolve, butyl cellosolve or cellosolve acetate, ethers such as dioxane or tetrahydrofuran, and the like. In a case of the mixed solvent, the amount of alcohol to the other solvents is preferably 80% by weight or more, and more preferably 90% by weight or more.

Examples of the alcohol include lower alcohols, such as methanol or ethanol.

On the other hand, the alkali catalyst is a catalyst used for promoting the respective reactions of the organic metal compounds (hydrolysis reaction or condensation reaction), and examples thereof include a basic catalyst such as ammonia, urea, monoamine or a quaternary ammonium salt, and ammonia is particularly preferred.

The concentration (content) of the alkali catalyst is from 0.6 mol/L to 0.85 mol/L, preferably from 0.63 mol/L to 0.78 mol/L, and more preferably from 0.66 mol/L to 0.75 mol/L.

When the concentration of the alkali catalyst is less than 0.6 mol/L, the dispersibility of the generated nuclear particles during the growth may become unstable. As a result, coarse aggregates such as secondary aggregates may be generated or a gel may be formed, and the particle size distribution may deteriorate in some cases.

On the other hand, when the concentration of the alkali catalyst is greater than 0.85 mol/L, stability of the generated nuclear particles may be excessively high. As a result, spherical nuclear particles may be generated and irregular shaped nuclear particles having an average degree of circularity of 0.85 or less may not be obtained. Accordingly, irregular shaped silica composite particles may not be obtained.

In addition, the concentration of the alkali catalyst is a concentration relative to the alcohol catalyst solution (alkali catalyst+solvent containing alcohol).

Next, a particle generating step will be described.

The particle generating step is a step of generating the silica composite particles by supplying an organic metal mixed solution and an alkali catalyst to an alkali catalyst solution, respectively, and allowing organic metal compounds to react, respectively, in the alkali catalyst solution (hydrolysis reaction or condensation reaction).

In this particle generating step, the silica composite particles are formed by generating nuclear particles by the respective reactions of the organic metal compounds at an early stage of supplying the organic metal mixed solution (nuclear particles generation stage) and growing the nuclear particles (nuclear particles growth stage).

In the organic metal compounds (a mixed solution of tetraalkoxysilane and the organic titanium compound) to be supplied to the alkali catalyst solution, the ratio of tetraalkoxysilane and the organic titanium compound (the organic titanium compound/tetraalkoxysilane) is suitably from 9.0 to 99999, preferably from 10.1 to 9999, and more preferably from 19 to 999 in a weight ratio.

In the organic metal mixed solution, when there is too little organic titanium compound, the content of titanium in the silica composite particles becomes lower. On the other hand, when there is too much organic titanium compound, the content of the titanium in silica composite particles becomes higher.

In particular, when there is too much organic titanium compound, this causes the vigorous reaction of the organic titanium compound, which leads to excess occurrence of coarse powder or the deterioration of particle size distribution and of the shape; thereby the desired particle size is unable to be obtained. In particular, in a case where a mechanical load is applied to the obtained silica composite particles, the particles tend to have defects, and it is difficult to have an improvement in fluidity maintenance.

Examples of the tetraalkoxysilane include tetramethoxysilane, tetraethoxysilane, tetrapropoxysilane, and tetrabutoxysilane. From the viewpoint of controllability of reaction rate, or the shape, the particle size, the particle size distribution, and the like of the silica composite particles to be obtained, tetramethoxysilane and tetraethoxysilane are preferred.

The organic titanium compound is an organic metal compound in which a titanium atom is coupled to an organic group through oxygen (oxygen atom), and examples thereof include organic titanium compounds such as alkoxides (for example, methoxide, ethoxide, n-propoxide, i-propoxide, n-butoxide, i-butoxide, sec-butoxide, tert-butoxide, and the like) and chelates or acrylates (for example, β-diketones such as acetyl acetate; β-ketoesters such as ethyl acetoacetate; amines such as triethanoleamine; carboxylic acids such as acetic acid, butyric acid, lactic acid, and citric acid; and the like).

However, the organic titanium compound is preferably an organic titanium compound having one or more (preferably two or more) alkoxy groups in terms of the controllability of the reaction rate or the shape, particle diameter, particle size distribution, and the like of the obtained silica composite particles. That is, the organic titanium compound is preferably an organic titanium compound in which one or more (preferably two or more) alkoxy groups (alkyl groups bonded to a titanium atom through oxygen (oxygen atoms)) are bonded to a titanium atom.

In addition, the number of carbon atoms in the alkoxy group is 8 or less, and preferably from 2 to 4 in terms of the controllability of the reaction rate or the shape, particle diameter, particle size distribution, and the like of the obtained silica composite particles.

Specific examples of the organic titanium compound include tetra-i-propoxy titanium, tetra-n-butoxy titanium, tetra-t-butoxy titanium, di-i-propoxy.bis(ethyl acetoacetate) titanium, di-i-propoxy.bis(acetylacetonate) titanium, di-i-propoxy bis(triethanolaminate)titanium, di-i-propoxy titanium.diacetate, and di-i-propoxy titanium.dipropionate.

The supply amount of the organic metal mixed solution is from 0.001 mol/(mol·min) to 0.01 mol/(mol·min), preferably from 0.002 mol/(mol·min) to 0.009 mol/(mol·min), and more preferably from 0.003 mol/(mol-min) to 0.008 mol/(mol·min), relative to the alcohol of the alkali catalyst solution.

This amount means that the organic metal compound is supplied in a supply amount of from 0.001 mol to 0.01 mol per one minute, relative to per 1 mol of the alcohol used in a step of preparing the alkali catalyst solution.

Furthermore, the particle size of the silica composite particles depends on the type of the organic metal compound or the reaction conditions, but primary particles having a particle size of 100 nm or more may be obtained by setting the total supply amount of the organic metal compound used in the reaction of the particles generation to be 1.08 mol or more, relative to 1 L of the dispersion of the silica composite particles and primary particles having a particle size of 500 nm or less may be obtained by setting the total supply amount of the organic metal compound to be 5.49 mol or less, relative to 1 L of the dispersion of the silica composite particles.

When the supply amount of the organic metal mixed solution is smaller than 0.001 mol/(mol·min), the contact probability between the organic metal compound added dropwise and the nuclear particles is further reduced. In this case, however, production efficiency is low because it takes a long time to complete the dropwise addition of the total supply amount of tetraalkoxysilane.

It is considered that when the supply amount of the organic metal mixed solution is 0.01 mol/(mol·min) or more, the reaction between the organic metal compounds may be caused before the organic metal compound added dropwise and the nuclear particles start to react with each other. Thus, since uneven distribution of an organic metal compound supplied to the nuclear particles may be exaggerated and the variation in formation of the nuclear particles may be caused, the average particle diameter and the distribution width of the shape distribution may be increased.

On the other hand, examples of the alkali catalyst to be supplied to the alkali catalyst solution include the substances as illustrated above. The alkali catalyst to be supplied may be the same as or different from the alkali catalyst that has been previously contained in the alkali catalyst solution, but is preferably the same as the alkali catalyst.

The supply amount of the alkali catalyst is from 0.1 mol to 0.4 mol, preferably from 0.14 mol to 0.35 mol, and more preferably from 0.18 mol to 0.30 mol, relative to 1 mol of a total supply amount of the organic metal compound (a total supply amount of the tetraalkoxysilane and the organic titanium compound) supplied per one minute.

When the supply amount of the alkali catalyst is less than 0.1 mol, dispersibility of the nuclear particles in the course of growth of the generated nuclear particles may become unstable. As a result, coarse aggregates such as secondary aggregates may be generated, or a gel may be formed, and thus, the particle size distribution may deteriorate.

On the other hand, when the supply amount of the alkali catalyst is greater than 0.4 mol, the generated nuclear particles are excessively stabilized, and even if irregular shaped nuclear particles are generated in the nuclear particle generation stage, the nuclear particles grow into a spherical shape during the nuclear particle growth stage, so that irregular shaped silica composite particles are not obtained.

Here, in the particle generating step, while the organic metal mixed solution and the alkali catalyst are supplied to the alkali catalyst solution, respectively, this supply method may be a method of continuously supplying the materials, or may be a method of intermittently supplying the materials.

Furthermore, in the particle generating step, the temperature of the alkali catalyst solution (temperature upon supply) is, for example, suitably in a range of from 5° C. to 50° C., preferably from 15° C. to 40° C.

Thus, the silica composite particles are obtained through the steps described above. In this state, the silica composite particles to be obtained are obtained in the form of a dispersion, but may be used as a dispersion of the silica composite particles as it is, or as a powder of the silica composite particles extracted by removing the solvent.

When the silica composite particles are used as a dispersion of silica composite particles, the solids concentration of silica composite particles may be adjusted by diluting the dispersion with water or alcohol or by concentrating the dispersion, as necessary. Furthermore, the dispersion of silica composite particles may be used by substituting the solvent with water-soluble organic solvents such as other alcohols, esters, or ketones.

On the other hand, when the silica composite particles are used as a powder, it is necessary to remove the solvent from the dispersion of the silica composite particles. Examples of the method for removing the solvent include known methods such as 1) a method of removing the solvent by filtration, centrifugal separation, distillation, and the like, and then drying the resultant by a vacuum dryer, a tray dryer, and the like, 2) a method of directly drying a slurry by a fluidized bed dryer, a spray dryer, and the like. The drying temperature is not particularly limited, but is preferably 200° C. or lower. When the drying temperature is above 200° C., it is likely to cause bonding among the primary particles or generation of coarse particles due to the condensation of silanol groups remaining on the silica composite particle surface.

The dried silica composite particles are preferably pulverized or sieved in order to remove coarse particles or aggregates therefrom, as necessary. The method of pulverization is not particularly limited and may be carried out by a dry pulverizer, such as a jet mill, a vibration mill, a ball mill, or a pin mill. The method of sieving may be carried out by known devices, such as a vibration sieve or a wind classifier.

The silica composite particles obtainable by the method of preparing the silica composite particles according to the exemplary embodiment may be used after having the surface of the silica composite particles treated with a hydrophobizing agent.

Examples of the hydrophobizing agent include known organosilicon compounds having an alkyl group (for example, a methyl group, an ethyl group, a propyl group, or a butyl group). Specific examples thereof include silazane compounds (for example, silane compounds, such as methyltrimethoxysilane, dimethyldimethoxysilane, trimethylcholorosilane, or trimethylmethoxysilane, hexamethyldisilazane, and tetramethyldisilazane). The hydrophobizing agents may used singly or in combination of two or more kinds thereof.

Among these hydrophobizing agents, organosilicon compounds having a trimethyl group, such as trimethylmethoxysilane or hexamethyldisilazane, are preferred.

The amount used of the hydrophobizing agent is not particularly limited, but in order to achieve the effect of hydrophobization, for example, the amount used is from 1% by weight to 100% by weight, and preferably from 5% by weight to 80% by weight, relative to the silica composite particles.

Examples of the method of obtaining a dispersion of hydrophobic silica composite particles which have been subjected to a hydrophobization treatment with a hydrophobizing agent include a method of obtaining a dispersion of hydrophobic silica composite particles by adding a required amount of a hydrophobizing agent to a dispersion of silica composite particles, allowing the same to react under stirring at a temperature in the range of from 30° C. to 80° C., and thereby subjecting the silica composite particles to a hydrophobization treatment. When this reaction temperature is lower than 30° C., it may be difficult for the hydrophobization reaction to proceed, and at a temperature exceeding 80° C., gelation of the dispersion due to the self-condensation of the hydrophobizing agent, or aggregation of the silica composite particles may be likely to occur.

On the other hand, examples of the method of obtaining a powder of hydrophobic silica composite particles include a method of obtaining a powder of hydrophobic silica composite particles by obtaining a dispersion of hydrophobic silica composite particles by the method as described above, and then drying the same by the method as described above; a method of obtaining a powder of hydrophobic silica composite particles by drying a dispersion of silica composite particles to obtain a powder of the hydrophilic silica composite particles, and then adding a hydrophobizing agent thereto to perform a hydrophobization treatment; and a method of obtaining a powder of hydrophobic silica composite particles by obtaining a dispersion of hydrophobic silica composite particles, and then drying the same to obtain a powder of the hydrophobic silica composite particles, and further adding a hydrophobizing agent thereto to perform a hydrophobization treatment.

Here, the examples of the method for hydrophobizing a powder of silica composite particles include a method which includes stirring a powder of hydrophilic silica composite particles in a treatment bath, such as a Henschel mixer, or a fluidized bed, adding the hydrophobizing agent thereto, and heating the treatment bath to gasify the hydrophobizing agent so as to react with silanol groups on the surface of the powder of silica composite particles. The treatment temperature is not particularly limited, but is, for example, preferably from 80° C. to 300° C., and more preferably from 120° C. to 200° C.

The silica composite particles according to the exemplary embodiment as described above may be applied in a variety of fields such as toners, cosmetics, or abrasives.

EXAMPLES

Hereinafter, the present invention will be more specifically described with reference to the Examples. However, these Examples are not intended to limit the scope of the invention. Unless otherwise specified, "parts" and "%" are on the weight basis.

Example 1

Alkali Catalyst Solution Preparing Step [Preparation of Alkali Catalyst Solution]

400 parts of methanol and 70 parts of 10% of ammonia water ($NH_4OH$) are placed in a 2.5 L glass reaction vessel equipped with a stirrer, a dropping nozzle and a thermometer, and mixed under stirring to obtain an alkali catalyst solution. At this time, the amount of ammonia catalyst: the amount of $NH_3$ ($NH_3$[mol]/($NH_3$+methanol+water) [L]) in the alkali catalyst solution is 0.71 mol/L.

Particles Forming Step [Preparation of Suspension of Silica Composite Particles]

First, 3.0% of tetrabutoxytitanium (TBT: tetra-t-butoxytitanium) relative to tetramethoxysilane (TMOS) is added as the organic titanium compound to prepare an organic metal mixed solution.

Subsequently, the temperature of the alkali catalyst solution is adjusted to 25° C., and the alkali catalyst solution is substituted with nitrogen. Thereafter, while stirring the alkali catalyst solution at 120 rpm, 200 parts of the organic metal mixed solution and 158 parts of ammonia water ($NH_4OH$) containing a catalyst ($NH_3$) at a concentration of 3.8% are started to be added dropwised to the alkali catalyst solution at the same time over 60 minutes in the following supply amounts, to obtain a suspension of silica composite particles (a silica composite particles suspension).

At this time, the supply amount of the organic metal mixed solution is adjusted to be 0.0017 mol/(mol·min), relative to the total number of moles of methanol in the alkali catalyst solution.

In addition, the supply amount of 3.8% ammonia water is adjusted to be 0.27 mol/min, relative to 1 mol of a total supply amount of the organic metal compound (tetraalkoxysilane and tetrabutoxytitanium) supplied per one minute.

Thereafter, 300 parts of the solvent of the obtained silica composite particles suspension is distilled off by heating and distillation, 300 parts of pure water is added to the residue, and then the solution thus obtained is dried by a freeze dryer to obtain irregular shaped hydrophilic silica composite particles.

Hydrophobization Treatment of Silica Composite Particles

Furthermore, 7 parts of hexamethyldisilazane is added to 35 parts of the hydrophilic silica composite particles, and the mixture is allowed to react for 2 hours at 150° C., thereby obtaining irregular shaped hydrophobic silica composite particles having a hydrophobized particle surface.

Examples 2 to 17, and Comparative Examples 1 to 9

Irregularly shaped hydrophobic silica composite particles are obtained in the same manner as Example 1, except that various conditions in the alkali catalyst solution preparing step and the particle generating step, are changed as indicated in Table 1.

At this time, the organic metal mixed solution is prepared by adding the organic titanium compound (tetrabutoxytitanium (TBT) or the like) to tetramethoxysilane (TMOS), according to the ratio of the total supply amount of tetramethoxysilane (TMOS) and the total supply amount of the organic titanium compound (tetrabutoxytitanium (TBT) or the like) as shown in Table 1.

In addition, in Example 14, hydrophobic silica composite particles are obtained using titanium diisopropoxy bis(acetylacetonate) (OLGATIX TC-100 manufactured by Matsumoto Fine Chemical Co., Ltd.) instead of tetrabutoxytitanium (TBT).

In Example 15, hydrophobic silica composite particles are obtained using titanium tetra acetylacetonate (OLGATIX TC-401 manufactured by Matsumoto Fine Chemical Co., Ltd.) instead of tetrabutoxytitanium (TBT).

In Example 16, hydrophobic silica composite particles are obtained using titaniumdi-2-ethylhexyloxybis(2-ethyl-3-hydroxyhexyloxide) (OLGATIX TC-200 manufactured by Matsumoto Fine Chemical Co., Ltd.) instead of tetrabutoxytitanium (TBT).

In Example 17, hydrophobic silica composite particles are obtained using titanium diisopropoxy bis(ethylacetoacetate) (OLGATIX TC-750 manufactured by Matsumoto Fine Chemical Co., Ltd.) instead of tetrabutoxytitanium (TBT).

Evaluation

Properties of Silica Composite Particles

For the hydrophobic silica composite particles obtained from each Example, the content of titanium, the average particle diameter, particle size distribution, and the average degree of circularity are investigated according to the methods previously described.

Furthermore, for the hydrophobic silica composite particles obtained from Examples 1 to 17, and Comparative Examples 2 to 9, a titanium content is quantified by the NET strength of constitutional elements in the particles, using a fluorescence X-ray analyzer: XRF 1500 (manufactured by Shimadzu Corporation), and then mapping is performed with an SEM-EDX (manufactured by Hitachi Ltd., S-3400N). As a result of the investigation, it is confirmed that titanium is present in a dispersed state in silica composite particles.

Dispersibility

In a case where the hydrophobic silica composite particles obtained from each Example are dispersed in the resin particle, the dispersibility of the hydrophobic silica composite particles in resin particles is evaluated.

Specifically, hydrophobic silica composite particles are left to stand under an environment of normal temperature and normal humidity (under an environment of a temperature of 25° C. and a humidity of 55% RH) for 17 hours, and then 0.01 g of hydrophobic silica composite particles are added to 6 g of resin particles having a particle size of 100 μm, and the same is mixed by shaking with a shaking apparatus for 5 minutes, and then the surface of the resin particles is observed with an SEM apparatus, and evaluated in accordance with the following evaluation criteria.

Furthermore, the cases where the hydrophobic silica composite particles are left to stand under an environment of a high temperature and a high humidity (under an environment of a temperature of 30° C. and a humidity of 85% RH), and under an environment of a low temperature and a low humidity (under an environment of a temperature of 10° C. and a humidity of 15% RH), for 17 hours, are also evaluated in the same way.

Evaluation Criteria (Dispersibility)

A: silica composite particles are uniformly dispersed on the surface of resin particles.

B: A slight degree of aggregates of silica composite particles are observed, but the coverage (coverage amount) into the surface of resin particles is not lowered. Acceptable for practical applications.

C: Aggregates of silica composite particles are partially observed, and the coverage (coverage amount) into the surface of resin particles is clearly lowered. Poor Dispersion.

Fluidity Maintenance

In a case where the hydrophobic silica composite particles obtained from each Example are dispersed in the resin particles, the maintenance of fluidity of the resin particle is evaluated.

Specifically, hydrophobic silica composite particles are left to stand under an environment of a high temperature and a high humidity (under an environment of a temperature of 30° C. and a humidity of 85% RH) for 17 hours, and then 0.1 g of hydrophobic silica composite particles are added to 2 g of resin particles having a particle size of 10 μm, and the same is mixed by shaking with a shaking apparatus for 25 minutes. Thereafter, the resin particles are placed on a 75-μm sieve and vibrated at a vibration width of 1 mm for 90 seconds, and the state of the resin particles falling down is observed and evaluated in accordance with the following evaluation criteria.

Furthermore, the case where hydrophobic silica composite particles are left to stand under an environment of a low temperature and a low humidity (under an environment of a temperature of 10° C. and a humidity of 15% RH), for 17 hours, is also evaluated in the same way.

—Evaluation Criteria (Fluidity)—

A: Resin particles do not remain on the sieve.

B: A slight amount of resin particles remain on the sieve.

C: A significant amount of resin particles remain on the sieve.

TABLE 1

| | Alkali catalyst solution preparing step (alkali catalyst solution composition) | | | | | | Particle generating step (organic metal mixed solution and ammonia water supply conditions) Total supply |
|---|---|---|---|---|---|---|---|
| | methanol Number of parts | 10% ammonia water Number of parts | Number of moles of methanol mol | Number of moles of $NH_3$ mol | Solvent volume L | $NH_3$ amount mol/L | amount of organic metal mixed solution Number of parts |
| Example 1 | 400 | 70 | 12.5 | 0.41 | 582.32 | 0.71 | 200 |
| Example 2 | 400 | 70 | 12.5 | 0.41 | 582.32 | 0.71 | 200 |
| Example 3 | 400 | 75 | 12.5 | 0.44 | 587.87 | 0.75 | 200 |
| Example 4 | 400 | 60 | 12.5 | 0.35 | 571.21 | 0.62 | 80 |
| Example 5 | 400 | 60 | 12.5 | 0.35 | 571.21 | 0.62 | 780 |
| Example 6 | 400 | 65 | 12.5 | 0.38 | 576.76 | 0.66 | 200 |
| Example 7 | 400 | 58 | 12.5 | 0.34 | 568.99 | 0.60 | 200 |
| Example 8 | 400 | 85 | 12.5 | 0.50 | 598.99 | 0.83 | 200 |
| Example 9 | 400 | 70 | 12.5 | 0.41 | 582.32 | 0.71 | 200 |
| Example 10 | 400 | 70 | 12.5 | 0.41 | 582.32 | 0.71 | 200 |
| Example 11 | 400 | 70 | 12.5 | 0.41 | 582.32 | 0.71 | 135 |
| Example 12 | 400 | 70 | 12.5 | 0.41 | 582.32 | 0.71 | 1150 |
| Example 13 | 400 | 60 | 12.5 | 0.35 | 571.21 | 0.62 | 35 |
| Example 14 | 400 | 70 | 12.5 | 0.41 | 582.32 | 0.71 | 200 |
| Example 15 | 400 | 70 | 12.5 | 0.41 | 582.32 | 0.71 | 200 |
| Example 16 | 400 | 70 | 12.5 | 0.41 | 582.32 | 0.71 | 200 |
| Example 17 | 400 | 70 | 12.5 | 0.41 | 582.32 | 0.71 | 200 |

| | Particle generating step (organic metal mixed solution and ammonia water supply conditions) | | | | | |
|---|---|---|---|---|---|---|
| | Total supply amount of TMOS Number of parts | Total supply amount of organic titanium compound Number of parts | Supply amount of organic metal compound [supply amount relative to number of moles of alcohol of alkali catalyst solution] mol/mol · min | Drop-wise addition time min | Total supply amount of ammonia water Parts by weight | Supply amount of $NH_3$ [mol(number of moles relative to 1 mole of total supply amount of organic metal compound supplied per one minute)] mol/mol |
| Example 1 | 194 | 6 | 0.0017 | 60 | 158 | 0.27 |
| Example 2 | 180 | 20 | 0.0016 | 60 | 158 | 0.27 |
| Example 3 | 200 | 0.2 | 0.0017 | 60 | 158 | 0.35 |
| Example 4 | 78 | 2 | 0.0007 | 60 | 63 | 0.27 |
| Example 5 | 757 | 23 | 0.0066 | 60 | 616 | 0.27 |
| Example 6 | 188 | 12 | 0.0016 | 60 | 158 | 0.27 |
| Example 7 | 194 | 6 | 0.0017 | 60 | 158 | 0.27 |
| Example 8 | 194 | 6 | 0.0017 | 60 | 158 | 0.27 |
| Example 9 | 194 | 6 | 0.0017 | 60 | 158 | 0.11 |

TABLE 1-continued

| | | | | | | |
|---|---|---|---|---|---|---|
| Example 10 | 194 | 6 | 0.0017 | 60 | 158 | 0.39 |
| Example 11 | 131 | 4 | 0.0011 | 60 | 107 | 0.27 |
| Example 12 | 1116 | 35 | 0.0097 | 60 | 909 | 0.27 |
| Example 13 | 34 | 1 | 0.0010 | 18 | 28 | 0.27 |
| Example 14 | 194 | 6 | 0.0017 | 60 | 158 | 0.27 |
| Example 15 | 194 | 6 | 0.0017 | 60 | 158 | 0.27 |
| Example 16 | 194 | 6 | 0.0017 | 60 | 158 | 0.27 |
| Example 17 | 194 | 6 | 0.0017 | 60 | 158 | 0.27 |

TABLE 2

| | Alkali catalyst solution preparing step (alkali catalyst solution composition) | | | | | | Particle generating step (organic metal mixed solution and ammonia water supply conditions) Total supply |
|---|---|---|---|---|---|---|---|
| | methanol Number of parts | 10% ammonia water Number of parts | Number of moles of methanol mol | Number of moles of $NH_3$ mol | Solvent volume L | $NH_3$ amount mol/L | amount of organic metal mixed solution Number of parts |
| Comparative example 1 | 400 | 70 | 12.5 | 0.41 | 582.32 | 0.71 | 200 |
| Comparative example 2 | 400 | 70 | 12.5 | 0.41 | 582.32 | 0.71 | 200 |
| Comparative example 3 | 400 | 60 | 12.5 | 0.35 | 571.21 | 0.62 | 72 |
| Comparative example 4 | 400 | 60 | 12.5 | 0.35 | 571.21 | 0.62 | 910 |
| Comparative example 5 | 400 | 60 | 12.5 | 0.35 | 571.21 | 0.58 | 200 |
| Comparative example 6 | 400 | 50 | 12.5 | 0.29 | 560.10 | 0.58 | 200 |
| Comparative example 7 | 400 | 90 | 12.5 | 0.53 | 604.54 | 0.88 | 200 |
| Comparative example 8 | 400 | 70 | 12.5 | 0.41 | 582.32 | 0.71 | 1250 |
| Comparative example 9 | 400 | 60 | 12.5 | 0.35 | 571.21 | 0.62 | 80 |

| | Particle generating step (organic metal mixed solution and ammonia water supply conditions) | | | | | |
|---|---|---|---|---|---|---|
| | Total supply amount of TMOS Number of parts | Total supply amount of organic titanium compound Number of parts | Supply amount of organic metal compound [supply amount relative to number of moles of alcohol of alkali catalyst solution] mol/mol · min | Dropwise addition time min | Total supply amount of ammonia water Parts by weight | Supply amount of $NH_3$ [mol(number of moles relative to 1 mole of total supply amount of organic metal compound supplied per one minute)] mol/mol |
| Comparative example 1 | 200 | 0 | 0.0018 | 60 | 158 | 0.27 |
| Comparative example 2 | 176 | 24 | 0.0015 | 60 | 158 | 0.27 |
| Comparative example 3 | 70 | 2 | 0.0006 | 60 | 57 | 0.27 |
| Comparative example 4 | 883 | 27 | 0.0077 | 60 | 719 | 0.27 |
| Comparative example 5 | 194 | 6 | 0.0017 | 60 | 158 | 0.20 |
| Comparative example 6 | 194 | 6 | 0.0017 | 60 | 158 | 0.09 |
| Comparative example 7 | 194 | 6 | 0.0017 | 60 | 158 | 0.41 |
| Comparative example 8 | 1213 | 38 | 0.0106 | 60 | 988 | 0.27 |
| Comparative example 9 | 78 | 2 | 0.0027 | 15 | 63 | 0.27 |

TABLE 3

| | Properties of silica composite particles | | | | Evaluation |
|---|---|---|---|---|---|
| | Content of titanium [%] | Average particle diameter D50v [nm] | Particle size distribution [−] | Average degree of circularity [−] | Dispersibility Under environment of room temperature and normal humidity |
| Example 1 | 3.0 | 160 | 1.34 | 0.72 | A |
| Example 2 | 9.8 | 150 | 1.42 | 0.54 | B |
| Example 3 | 0.1 | 165 | 1.12 | 0.82 | A |
| Example 4 | 3.0 | 70 | 1.25 | 0.8 | A |
| Example 5 | 3.0 | 450 | 1.27 | 0.83 | A |
| Example 6 | 5.8 | 155 | 1.38 | 0.66 | A |
| Example 7 | 3.0 | 157 | 1.39 | 0.62 | B |
| Example 8 | 3.0 | 165 | 1.29 | 0.85 | B |
| Example 9 | 3.0 | 160 | 1.35 | 0.7 | A |
| Example 10 | 3.0 | 158 | 1.31 | 0.81 | B |
| Example 11 | 3.0 | 161 | 1.32 | 0.78 | A |
| Example 12 | 3.0 | 498 | 1.28 | 0.62 | B |
| Example 13 | 3.0 | 35 | 1.38 | 0.65 | A |
| Example 14 | 2.8 | 158 | 1.33 | 0.77 | A |
| Example 15 | 1.7 | 155 | 1.33 | 0.71 | A |
| Example 16 | 2.3 | 157 | 1.31 | 0.67 | A |
| Example 17 | 2.4 | 162 | 1.31 | 0.7 | A |

| | Evaluation | | | |
|---|---|---|---|---|
| | Dispersibility | | Maintenance of fluidity | |
| | Under environment of high temperature and high humidity | Under environment of low temperature and low humidity | Under environment of high temperature and high humidity | Under environment of low temperature and low humidity |
| Example 1 | A | A | A | A |
| Example 2 | B | B | B | A |
| Example 3 | A | A | A | B |
| Example 4 | A | A | B | A |
| Example 5 | A | A | B | A |
| Example 6 | A | B | A | A |
| Example 7 | B | B | A | A |
| Example 8 | B | B | A | A |
| Example 9 | A | A | A | A |
| Example 10 | B | B | A | A |
| Example 11 | A | A | A | A |
| Example 12 | B | B | B | A |
| Example 13 | A | A | B | A |
| Example 14 | A | A | A | A |
| Example 15 | A | A | A | A |
| Example 16 | A | A | A | A |
| Example 17 | A | A | A | A |

TABLE 4

| | | | | | Evaluation | | | | |
|---|---|---|---|---|---|---|---|---|---|
| | Properties of silica composite particles | | | | Dispersibility | | | Maintenance of fluidity | |
| | Content of titanium [%] | Average particle diameter D50v [nm] | Particle size distribution [−] | Average degree of circularity [−] | Under environment of room temperature and normal humidity | Under environment of high temperature and high humidity | Under environment of low temperature and low humidity | Under environment of high temperature and high humidity | Under environment of low temperature and low humidity |
| Comparative example 1 | 0.0 | 165 | 1.29 | 0.81 | A | A | B | A | C |
| Comparative example 2 | 12.0 | Bimodal broad | | | Not evaluated | | | | |
| Comparative example 3 | 3.0 | 50 | 1.22 | 0.9 | B | B | B | C | A |
| Comparative example 4 | 3.0 | 550 | 1.21 | 0.82 | C | C | C | C | A |
| Comparative example 5 | 3.0 | 135 | 1.55 | 0.53 | C | C | C | B | A |

TABLE 4-continued

| | Properties of silica composite particles | | | | Evaluation | | | | |
|---|---|---|---|---|---|---|---|---|---|
| | | | | | Dispersibility | | | Maintenance of fluidity | |
| | Content of titanium [%] | Average particle diameter D50v [nm] | Particle size dis-tribution [−] | Average degree of circularity [−] | Under environment of room temperature and normal humidity | Under environment of high tem-perature and high humidity | Under environment of low temperature and low humidity | Under environment of high temperature and high humidity | Under environment of low temperature and low humidity |
| Comparative example 6 | 3.0 | Gelation | | | Evaluation unavailable | | | | |
| Comparative example 7 | 3.0 | 162 | 1.12 | 0.92 | C | C | C | C | A |
| Comparative example 8 | 3.0 | 510 | 1.25 | 0.58 | C | C | C | B | A |
| Comparative example 9 | 3.0 | 28 | 1.4 | 0.61 | B | B | B | C | C |

From the above results, it is seen that the present Examples exhibit lower temperature and humidity environmental dependency in dispersibility and maintenance of fluidity as compared with the Comparative Examples.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A method of preparing silica composite particles comprising:

preparing an alkali catalyst solution containing an alkali catalyst at a concentration of from 0.6 mol/L to 0.85 mol/L, in a solvent containing alcohol; and supplying, into the alkali catalyst solution:

a mixed solution of tetraalkoxysilane and an organic titanium compound in which an organic group is coupled to a titanium atom through oxygen at a supply amount of from 0.001 mol/(mol·min) to 0.01 mol/(mol·min) relative to the alcohol, and an alkali catalyst at a supply amount of from 0.1 mol to 0.4 mol, relative to 1 mol of a total supply amount of the tetraalkoxysilane and the organic titanium compound supplied per one minute.

2. The method of preparing silica composite particles according to claim 1, wherein the concentration of the alkali catalyst is from 0.63 mol/L to 0.78 mol/L.

3. The method of preparing silica composite particles according to claim 1, wherein the concentration of the alkali catalyst is from 0.66 mol/L to 0.75 mol/L.

4. The method of preparing silica composite particles according to claim 1, wherein the supply amount of the mixed solution of the tetraalkoxysilane and the organic titanium compound is from 0.002 mol/(mol·min) to 0.009 mol/(mol·min) relative to the alcohol of the alkali catalyst solution.

5. The method of preparing silica composite particles according to claim 1, wherein the supply amount of the mixed solution of the tetraalkoxysilane and the organic titanium compound is from 0.003 mol/(mol·min) to 0.008 mol/(mol·min) relative to the alcohol of the alkali catalyst solution.

6. The method of preparing silica composite particles according to claim 1, wherein the supply amount of the alkali catalyst is from 0.14 mol to 0.35 mol relative to 1 mol of the total supply amount of the tetraalkoxysilane and the organic titanium compound supplied per one minute.

7. The method of preparing silica composite particles according to claim 1, wherein the supply amount of the alkali catalyst is from 0.18 mol to 0.30 mol relative to 1 mol of the total supply amount of the tetraalkoxysilane and the organic titanium compound supplied per one minute.

* * * * *